United States Patent [19]

de Cooker et al.

[11] 4,181,801

[45] Jan. 1, 1980

[54] PROCESS FOR PREPARING CYANURIC ACID

[75] Inventors: Mario G. R. T. de Cooker; Anita G. W. G. Haemers, both of Geleen, Netherlands

[73] Assignee: Stamicarbon, B.V., Geleen, Netherlands

[21] Appl. No.: 903,400

[22] Filed: May 8, 1978

[30] Foreign Application Priority Data

May 9, 1977 [NL] Netherlands .................. 7705050

[51] Int. Cl.$^2$ ............................................ C07D 251/32
[52] U.S. Cl. ................................................ 544/192
[58] Field of Search ........................................ 544/192

[56] References Cited

U.S. PATENT DOCUMENTS 4,118,570  10/1978  Brennan ..................... 544/192

*Primary Examiner*—John M. Ford
*Attorney, Agent, or Firm*—Cushman, Darby & Cushman

[57] ABSTRACT

An improved process for the preparation of cyanuric acid from urea/biuret. The cyanuric acid mass comprised of cyanuric acid and retained residual solvent is discharged from the reaction vessel and is fed to a heated fluidized bed of cyanuric acid particles for the removal of residual retained solvent.

9 Claims, 1 Drawing Figure

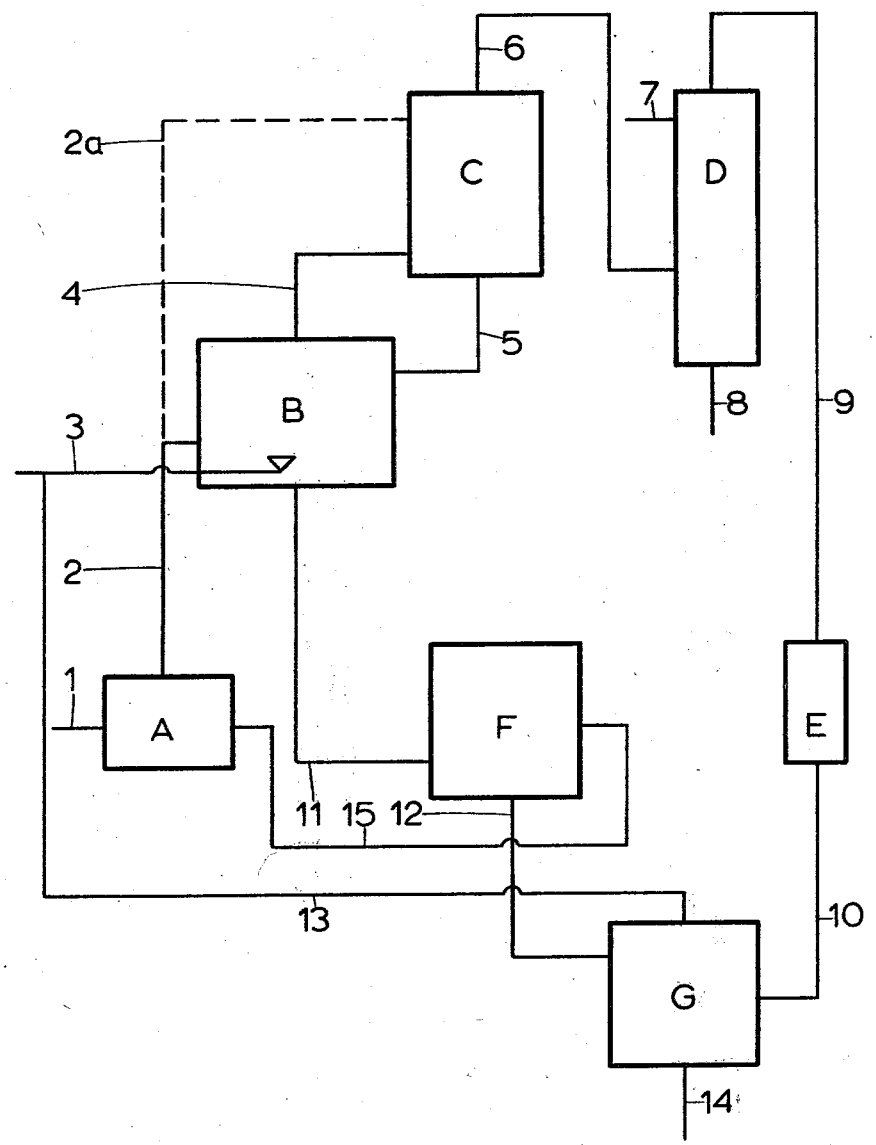

PROCESS FOR PREPARING CYANURIC ACID

The present invention relates to a process for preparing cyanuric acid by heating urea and/or biuret in a solvent. Preferably, the reaction mixture is being stripped with a stripping gas while being heated. A process of this general type is disclosed in Netherlands Patent Applications Nos. 69.10466 and 75.08098.

Application No. 69.10466 corresponds to U.S. Pat. No. 3,635,968 and British Pat. No. 1,265,549. Application 75.08098 corresponds to U.S. application Ser. No. 703,655, filed on July 8, 1976, to Schouteten et al, now abandoned and continued as Ser. No. 890,912, filed Mar. 27, 1978. Both of these references are illustrative and merely relate to the synthesis step. They are not concerned at all with the purification and isolation of the cyanuric acid.

BACKGROUND OF THE INVENTION

The known process results in a suspension of cyanuric acid in the solvent which may also contain dissolved unconverted urea and/or biuret. The cyanuric acid is then separated from the suspension by filtration, precipitation and decantation, centrifugation, or any other suitable method, but because the cyanuric acid will retain traces of solvent, the cyanuric acid as separated is a lumpy sticky mass with poor flow properties. Pure cyanuric acid can be obtained from this lumpy sticky product by washing it with a washing liquid such as water, but the washing causes losses as some cyanuric acid is dissolved in the water. Moreover, wet cyanuric acid crystals are obtained which then have to be dried.

It is therefore an objective of the present invention to remove this retained residual solvent from the cyanuric acid without having to wash the cyanuric acid with the attended loss of product and need for drying.

DESCRIPTION OF THE INVENTION

It has been discovered that, in spite of the poor flow properties of the sticky cyanuric acid solvent mass, the solvent can be removed from this mass in a continuous process by feeding the mass to a fluidized bed of cyanuric acid particles which is kept fluid with a flow of an inert gas and from which cyanuric acid particles are withdrawn either continuously or intermittently. In this manner, it is possible to obtain free flowing cyanuric acid crystals in one step without the need for washing and without losing any of the cyanuric acid.

Accordingly, in the present invention, cyanuric acid is prepared by heating urea and/or biuret in a suitable solvent in a reactor, with the resultant cyanuric acid solvent mass from the reaction mixture being fed to a fluidized bed of cyanuric acid particles which is kept fluid with a flow of inert gas while purified cyanuric acid particles are being withdrawn from the fluidized bed.

There is a method disclosed in British patent specification No. 1,344,926 which subjects a cyanuric acid powder digested with an aqueous acid solution and which still contains traces of an inorganic acid to a treatment with a gas containing ammonia or an amine in order to neutralize the traces of acid and remove the water. This process, however, is clearly distinguishable from the process according to the invention. In the process according to the present invention the cyanuric acid mass fed to the fluid bed has not been digested with an aqueous acid solution, so that no traces of an inorganic acid need be neutralized. Moreover, it is not necessary to remove water from the cyanuric acid mass. It should furthermore be noted that water is completely unsuitable as the solvent in the conversion of urea and/or biuret into cyanuric acid, as serious hydrolysis of urea, biuret and/or cyanuric acid would occur at the reaction temperature. On the other hand, the cyanuric acid mass does contain traces of the solvent with a high boiling point, which are not present in the known process.

In the process according to the present invention a solvent is used in which the urea and/or biuret are relatively much more soluble than cyanuric acid. The solvent must be thermally stable under the reaction conditions and should preferably be chemically inert. The solvent must have a sufficiently high boiling point in order to maintain a liquid phase during the reaction. Suitable solvents are, e.g., dialkyl sulphones or cyclic sulphones with at most 12 carbon atoms, halogen-substituted cresols and phenols, pyrrolidones and urethanes N-substituted with phenyl or alkyl groups with at most 6 carbon atoms, cyclic urethanes, polyether alcohols and cyclic polyethers and cyclohexanol or substituted cyclohexanols with one or more hydrocarbon groups with at most 6 carbon atoms as substituents. The hydrocarbon groups are preferably phenyl-, alkyl- or cycloalkyl groups. Examples of suitable solvents are dimethyl sulphone, dipropyl sulphone, sulpholane, chlorocresols, 5-methyl-2-oxazolidinone, diethylene-glycol monomethyl ether, diethylene-glycol diethyl ether, 2-methyl cyclohexanol, 2,6-dimethyl cyclohexanol and 2,4,6-trimethyl cyclohexanol. Sulpholane or a derivative of it substituted with one or more methyl groups are particularly suitable. Other suitable solvents are molten ammonium salts, provided they are sufficiently volatile at the temperature of the fluid bed treatment.

A catalyst, for example, an acid that is soluble in the reaction medium or an anhydride or ammonium salt of such an acid may be incorporated in the reaction mixture.

An ammonium-, alkali metal- or alkaline-earth metal nitrate may also be present in order to reduce the coproduction of ammelide and ammeline as disclosed in the co-pending application of De Cooker and Haemers Ser. No. 903,399, filed on May 8, 1978.

The reaction temperature usually ranges between about 150° and about 280° C., and is preferably between about 170° and about 220° C., with even better results obtained between about 175° and about 200° C. At higher temperatures, the reaction proceeds quicker, but the possibilities of forming more ammelide as a by-product, and of decomposing the solvent become greater.

The reaction pressure may range, e.g., between about 0.01 and about 10 atm. The reaction can preferably be conducted at about atmospheric pressure, e.g., a pressure of between 0.5 and 2 atmospheres. If it is intended to reduce the partial ammonia pressure by suction, the reaction pressure should preferably be between about 0.01 and about 0.25 atm.

The concentration of starting urea and/or biuret must be limited, otherwise the ammelide content of the cyanuric acid product will be increased to an unacceptable level. Concentrations of up to about 750 grams per kg of solution are preferred, but even higher urea and/or biuret concentrations may also be used. While at very low concentrations an excellent product is obtained, the costs per unit product are high. Preferably, the starting concentration of urea and/or biuret should range between about 150 and about 500 grams per kg of solution.

The fluidized bed is kept fluidized with a flow of an inert gas. Suitable gases are, for example, nitrogen, carbon dioxide, and gaseous hydrocarbons, preferably with 3–12 carbon atoms per molecule, such as toluene, xylenes or cyclohexane.

The temperature in the fluidized bed should be in the range of about 25° to about 300° C., with a preferred temperature ranging between about 150° and about 250° C. The pressure may be atmospheric, or, if desired, lower or higher than atmospheric pressure, for example between about 0.01 and about 10 atm.

One particularly suitable embodiment of the process of the present invention uses the vent gas from the fluidized bed as the stripping gas in the reactor. This embodiment provides several process advantages. Use of the vented gas from the fluidized bed, causes an unexpected higher rate of conversion of the urea and/or biuret into cyanuric acid while eliminating the need to treat the vended inert gas that is contaminated with traces of the solvent. Another process advantage is that the heat of fluidized bed is retained in the system without the need of additional heat exchange equipment.

It has also been discovered that the urea content of the cyanuric acid mass is unexpectedly reduced by incorporating water vapor in the inert gas that is fed to the fluidized bed. "Urea content" here also means the biuret and triuret contents of the cyanuric acid mass because the method of analysis used biuret and triuret are reported as urea. A very low urea content in the cyanuric acid is desirable for some applications, for example, in the preparation of chloroisocyanuric acid derivatives.

The water vapor concentration of the inert gas may range, e.g., between about 0.1% by volume and the saturation concentration. The temperature of the fluidized bed is the same as if the inert gas was free of water vapor.

DESCRIPTION OF THE DRAWING

One possible embodiment of a continuous process according to the present invention is shown diagrammatically in the drawing annexed.

Urea and/or biuret fed through conduit 1 to dissolver A, where the feed is dissolved in the solvent, for example, sulpholane. The solution flows through conduit 2 to reaction vessel B, where the conversion into cyanuric acid is conducted. A stripping gas, such as nitrogen, is fed to B through conduit 3. A gaseous mixture containing stripping gas, ammonia and solvent exits B through conduit 4 and is fed to condenser C. Condensed solvent flows back to B through conduit 5. Condencer C is preferably a scrubber, in which the washing liquid used may be a solution of urea and/or biuret in the solvent which is supplied through conduit 2a. Non-condensed gas exits C through conduit 6. This gas consists of a mixture of ammonia and stripping gas, from which ammonia can readily be recovered. In this embodiment, the non-condensed gas mixture from C is fed through conduit 6 to absorber D, in which the ammonia is washed with water supplied through conduit 7. An aqueous solution of ammonia is discharged through conduit 8. The non-condensed stripping gas passes through conduit 9, to heater E where it is heated to the necessary temperature and then through conduit 10 to the fluidized bed G.

A suspension of cyanuric acid in the solvent flows from reaction B through conduit 11 to separator F. Here, the cyanuric acid is separated off by filtration, precipitation and decantation, centrifugation, or in any other suitable manner. The solid product flows through conduit 12 to the fluidized bed G, where it is fed to a fluidized bed of cyanuric acid particles which are kept fluidized with a hot flow of an inert gas, such as nitrogen that is fed in through conduit 10. The vent gas from the fluidized bed is returned through conduit 13 to reactor B, where it is used as the stripping gas. Pure cyanuric acid is discharged through conduit 14. If desired, this product may be subjected to acid hydrolysis, e.g., with nitric acid, in a known way in order to hydrolyze the by-products ammelide and ammeline to cyanuric acid. If desired, the cyanuric acid product may also be subjected to a washing treatment, e.g., with water. The mother liquor that is separated off in F and which often still contains unconverted urea and/or biuret and is saturated with cyanuric acid flows back to dissolver A through conduit 15.

A predetermined amount of solvent is put in B at the start of the continuous process. The solvent and the inert gas are recycled with losses, if any, being made up somewhere in the recycling system. Solvent is preferably added in A and the inert gas is preferably added to the system through conduit 3.

EXAMPLE

The invention will be further elucidated by the following Example.

Urea dissolved in sulpholane was heated at a temperature of about 200° C. The urea concentration was 90 grams per kg of sulpholane. The retention time in the reactor was 1 hour. 240 liters (N.T.P.) of nitrogen per kg of sulpholane were passed through the reactor per hour with the nitrogen coming from the fluidized bed mentioned below.

The suspension exiting the reactor was passed to a continuous centrifuge in which the solid reaction product was separated. The liquid phase was returned to the reactor. The solid substance consisted of cyanuric acid containing 2.1% by weight of sulpholane and having a urea content (including biuret) of 0.23% by weight. It furthermore contains 0.5% of ammelide (the ammeline content was lower than the detection limit of the method of analysis). The solid substance had poor flow properties.

The solid substance was then fed to a fluidized bed of cyanuric acid particles which was fluidized with a flow of hot nitrogen. The fluidization rate was 30 liters (N.T.P.) of nitrogen per $cm^2$ of bed area per hour. The temperature was kept at about 200° C.

With a retention time of the cyanuric acid in the fluidized bed of 10 minutes, the sulpholane content dropped to 0.08% by weight and the urea content to 0.05% by weight. The product had excellent flow properties.

With a retention time in the fluidized bed of 60 minutes, a slightly purer cyanuric acid product was obtained with the sulpholane content being 0.07% by weight and the urea content 0.04% by weight. The product had excellent flow properties.

Various modifications of the process of the invention may be made without departing from the spirit or scope thereof and it should be understood that the invention is intended to be limited only as defined in the appended claims.

What is claimed is:

1. In a process for preparing cyanuric acid by heating at least one of urea and biuret in a suitable solvent in a reactor wherein the resultant solid cyanuric acid mass is separated from the reaction mixture, the improvement which comprises feeding the cyanuric acid mass which contains amounts of solvent to a fluidized bed of cyanuric acid particles which is fluidized with a flow of an inert gas and from which purified cyanuric acid particles are withdrawn.

2. The process of claim 1, wherein the solvent is selected from the dialkyl sulphones or cyclic sulphones with at most 12 carbon atoms, halogen-substituted cresols and phenols, pyrrolidones or urethanes N-substituted with phenyl or alkyl groups with at most 6 carbon atoms, cyclic urethanes, polyether alcohols and cyclic polyethers cyclohexanol or substituted cyclohexanols with one or more hydrocarbon groups with at most 6 carbon atoms as substituents, and molten ammonium salts.

3. The process of claim 2, wherein the solvent is sulpholane.

4. The process of claim 3, wherein the temperature in the fluid bed ranges between about 25° C. to about 300° C.

5. The process of claim 4, wherein the temperature in the fluid bed ranges between about 150° C. to about 250° C.

6. The process of claim 5, wherein the vent gas from the fluidized bed is used as a stripping gas in the reactor.

7. The process of claim 6, wherein ammonia is removed from the reactor vent gas and the vent gas is then fed to the fluidized bed.

8. The process of claim 7, wherein the inert gas fed to the fluidized bed contains water vapor.

9. An apparatus used in the preparation of cyanuric acid by heating at least one of urea and biuret in a suitable polar organic solvent comprising a reactor with feed lines for at least one of urea and biuret, solvent, and stripping gas, discharge line for vent gas to an absorber means to remove ammonia from said vent gas and a discharge line for cyanuric acid suspension to separator means, a gas conduit from said absorber for the removal of ammonia to a fluidized bed, a conduit for solid cyanuric acid mass from said separator means to said fluidized bed, a discharge line for vent/stripping gas to said reactor, a discharge line for solid cyanuric acid and a liquid line from said separator means to said reactor.

* * * * *